United States Patent
Tanigawara et al.

(10) Patent No.: US 8,809,362 B2
(45) Date of Patent: Aug. 19, 2014

(54) ANTICANCER AGENT SENSITIVITY-DETERMINING MARKER

(75) Inventors: Yusuke Tanigawara, Tokyo (JP); Tetsuya Suzuki, Tokyo (JP); Akito Nishimuta, Tokyo (JP); Shinji Sugimoto, Tokyo (JP); Yoshiaki Igarashi, Tokyo (JP)

(73) Assignees: Keio University, Tokyo (JP); Kabushiki Kaisha Yakult Honsha, Tokyo (JP)

( * ) Notice: Subject to any disclaimer, the term of this patent is extended or adjusted under 35 U.S.C. 154(b) by 37 days.

(21) Appl. No.: 13/505,175

(22) PCT Filed: Oct. 29, 2010

(86) PCT No.: PCT/JP2010/069364
§ 371 (c)(1),
(2), (4) Date: Apr. 30, 2012

(87) PCT Pub. No.: WO2011/052750
PCT Pub. Date: May 5, 2011

(65) Prior Publication Data
US 2012/0220618 A1 Aug. 30, 2012

(30) Foreign Application Priority Data

Oct. 30, 2009 (JP) .................. 2009-250258
Aug. 4, 2010 (JP) .................. 2010-175305

(51) Int. Cl.
| A61K 31/4375 | (2006.01) |
| A61P 35/00 | (2006.01) |
| A61K 31/4745 | (2006.01) |
| G01N 33/50 | (2006.01) |
| G01N 33/574 | (2006.01) |
| G01N 33/18 | (2006.01) |

(52) U.S. Cl.
CPC ........ *A61K 31/4745* (2013.01); *G01N 33/5011* (2013.01); *G01N 33/574* (2013.01); *G01N 33/18* (2013.01)
USPC ............... 514/283; 514/316; 546/48; 435/29; 435/6.14; 435/1.1; 435/40.5

(58) Field of Classification Search
CPC .......... A61K 31/4745; G01N 2500/00; G01N 2800/52; G01N 33/5011; G01N 33/574; G01N 33/6848
USPC .............. 514/283, 316; 546/48; 435/29, 6.14, 435/1.1, 40.5
See application file for complete search history.

(56) References Cited

U.S. PATENT DOCUMENTS

| 2010/0216131 A1* | 8/2010 | Luthra et al. ................ 435/6 |
| 2010/0323034 A1 | 12/2010 | Tanigawara et al. |
| 2011/0003842 A1 | 1/2011 | Tanigawara et al. |

FOREIGN PATENT DOCUMENTS

| WO | WO2008036691 | * 3/2008 | ........... G01N 33/574 |
| WO | 2009 096189 | 8/2009 | |
| WO | 2009 096196 | 8/2009 | |

OTHER PUBLICATIONS

Ohyama, T., et al., "Prediction of Anthracycline sensitivity by CDK profiling in combination with glutathione level," 67th Annual Meeting of the Japan Cancer Association, p. 390, P7009, (Sep. 20, 2008).

(Continued)

*Primary Examiner* — Savitha Rao
(74) *Attorney, Agent, or Firm* — Oblon, Spivak, McClelland, Maier & Neustadt, L.L.P.

(57) ABSTRACT

To provide a marker for determining sensitivity of a patient to an anti-cancer agent, and novel cancer therapeutic means employing the marker.
The marker for determining sensitivity to an anti-cancer agent is formed of one or more substances selected from the group consisting of a substance or a fragment thereof detected as an anion at m/z of 149.05 to 149.06, a substance or a fragment thereof detected as an anion at m/z of 152.99 to 153.00, a substance or a fragment thereof detected as a cation at m/z of 724.34 to 724.35, the peaks being determined by means of a mass spectrometer, glycerol 3-phosphate, dihydrobiopterin, GABA, lactic acid, asparagine, aspartic acid, 2-methylbutyroylcarnitine, 1-methyladenosine, and glutathione, and a substance involved in a metabolic pathway of any of these substances.

12 Claims, 9 Drawing Sheets

(56) References Cited

OTHER PUBLICATIONS

Shimada, Y., et al., "Phase II Study of C PT-11, a New Camptothecin Derivative, in Metastatic Colorectal Cancer," Journal of Clinical Oncology, vol. 11, No. 5, pp. 909-913, (May 1993).

Cunningham, D., et al., "A Phase III Study of Irinotecan (CPT-11) Versus Best Supportive Care in Patients With Metastatic Colorectal Caner Who Have Failed 5-Fuorouracil Therapy," vol. 26, No. 1, pp. 6-12, (Feb. 1999).

Rougier, P., et al., "Randomised trial of irinotecan versus fluorouracil by continuous infusion after fluorouracil failure in patients with metastatic colorectal cancer," The Lancet, vol. 352, pp. 1407-1412, (Oct. 31, 1998).

Pitot, H.C., et al., "N9841: A randomized phase III equivalence trial of irinotecan (CPT-11) versus oxaliplatin/5-fluorouracil (5FU)/leucovorin (FOLFOX4) in patients (pts) with advanced colorectal cancer (CRC) previously treated with 5FU," Journal of Clinical Oncology, vol. 23, No. 16S, Total 3 Pages, Abstract #3506, (Jun. 1, 2005).

Saltz, L.B., et al., "Irinotecan Plus Fuorouracil and Leucovorin for Metastatic Colorectal Cancer," New England Journal of Medicine, vol. 343, No. 13, pp. 905-914, (Sep. 28, 2000).

Douillard, J.Y., et al., "Irinotecan combined with fluorouracil compared with fluorouracil alone as first-line treatment for metastatic colorectal cancer: a multicentre randomised trial," The Lancet, vol. 355, pp. 1041-1047, (Mar. 25, 2000).

Kawato, Y., et al., "Intracellular Roles of SN-38, a Matabolite of the Camptothecin Derivative CPT-11, in the Antitumor Effect of CPT-11," Cancer Research, vol. 51, pp. 4187-4191, (Aug. 15, 1991).

Cecchin, E., et al., "Carboxylesterase Isoform 2 mRNA Expression in Peripheral Blood Mononuclear Cells Is a Predictive Marker of the Irinotecan to SN38 Activation Step in Colorectal Cancer Patients," Clinical Cancer Research, vol. 11, No. 19, pp. 6901-6907, (Oct. 1, 2005).

Tanimoto, K., et al., "Human carboxylesterase 1A2 expressed from carboxylesterase 1A1 and 1A2 genes is a potent predictor of CPT-11 cytotoxicity in vitro," Pharmacogenetics and Genomics, vol. 17, pp. 1-10, (2007).

Potti, A., et al., "Genomic signatures to guide the use of chemotherapeutics," Nature Medicine, vol. 12, No. 11, pp. 1294-1300, (Nov. 2006).

Sorensen, N.M., et al., "TIMP-1 Is Significantly Associated with Objective Response and Survival in Metastatic Colorectal Cancer Patients Receiving Combination of Irinotecan, 5-Fluorouracil, and Folinic Acid," Clinical Cancer Research, vol. 13, No. 14, pp. 4117-4122, (Jul. 15, 2007).

Paradiso, A., et al., "Topoisomerase-I, Thymidylate Synthase Primary Tumour Expression and Clinical Efficacy of 5-FU/CPT-11 Chemotherapy in Advanced Colorectal Cancer Patients," International Journal of Cancer, vol. 111, pp. 252-258, (2004).

International Search Report Issued Nov. 30, 2010 in PCT/JP10/69364 Filed Oct. 29, 2010.

U.S. Appl. No. 13/504,985, filed Apr. 30, 2012, Tanigawara, et al.
U.S. Appl. No. 13/505,143, filed Apr. 30, 2012, Tanigawara, et al.
U.S. Appl. No. 14/007,145, filed Sep. 24, 2013, Tanigawara, et al.

* cited by examiner

| Cell lines | IC$_{50}$ (nM) |
| --- | --- |
| HCT-15 | 6.21±1.46 |
| HCT-116 | 1.84±1.16 |
| HT-29 | 59.65±11.73 |
| Lovo | 7.89±6.06 |
| LS174T | 0.71±0.18 |
| SW480 | 10.20±11.28 |
| SW620 | 1.63±1.28 |
| WiDr | 63.27±10.95 |

Mean±S.D (n=3)

ANTICANCER AGENT SENSITIVITY-DETERMINING MARKER

TECHNICAL FIELD

The present invention relates to a marker for use in determination of the sensitivity of a cancer patient to an anti-cancer agent to be administered thereto, which marker can determine whether or not the cancer of the patient has a therapeutic response to the anti-cancer agent, and to application of the marker.

BACKGROUND ART

Anti-cancer agents have various types such as an alkylating agent, a platinum agent, an antimetabolite, an antitumor antibiotic, and an antitumor plant alkaloid. These anti-cancer agents are effective for some cancers but not effective for other cancers. Even when an anti-cancer agent is confirmed to be effective for a certain cancer, the anti-cancer agent is effective for some patients and not effective for other patients, leading to interindividual differences. Whether or not a cancer of a specific patient has response to an anti-cancer agent is designated as sensitivity to the anti-cancer agent.

Irinotecan hydrochloride (CPT-11) is an anti-cancer agent which has been developed in Japan and which has a mechanism of antitumor action based on the inhibition of topoisomerase I. In Japan, CPT-11 indicated for non-small-cell lung cancer, small cell lung cancer, cervical cancer, and ovarian cancer was approved as an effective drug in January, 1994. Further, CPT-11 indicated for gastric cancer, colorectal cancer, breast cancer, squamous cell carcinoma, and malignant lymphoma was approved in July, 1995. Currently, CPT-11 in multi-drug therapy has been recognized to be one of standard chemotherapy, in particular, as a first-line or a second-line for colorectal cancer all over the world, and CPT-11 had been established the efficacy (Non-Patent Documents 1 to 6).

Meanwhile, clinical performance (including survival rate) attained by chemotherapy for advanced or metastatic colorectal cancer has been drastically improved through a combination therapy employing a key drug such as CPT-11 or oxaliplatin, which launched in 1990s, and a fluoro-pyrimidine drug such as fluorouracil (5-FU), which had been a main drug for the colorectal cancer therapy. However, the response rate of such chemotherapy is as low as about 50%. That is, the chemotherapy is not effective for half of the patients to whom an anti-cancer agent has been administered, concomitant with risky severe adverse events. Thus, there is urgent demand for establishing a marker for predicting the sensitivity to an anti-cancer agent, which marker enables determination of interindividual therapeutic response (i.e., responder/non-responder).

Generally, the therapy schedule of cancer chemotherapy requires a long period of time. After repetition of several courses of chemotherapy while emergence of adverse events is carefully checked, attainment of a therapeutic effect and continuation of the therapy are assessed. The assessment requires a long period of time and high medical cost, and an adverse event has actually been observed to a certain degree. Thus, if there were means for predicting whether or not individual patients can receive the effect of chemotherapy before or in an early stage of the therapy, the burden on patients and emergence of adverse events can be reduced or mitigated, leading to reduction in medical cost.

Although CPT-11 itself has anti-tumor activity, CPT-11 is activated by carboxyl esterase in the body, to thereby be converted into 7-ethyl-10-hydroxycamptothecin (SN-38), which has an anti-tumor activity about 100 times to some thousand times that of CPT-11. Co-presence of CPT-11 and SN-38 is thought to provide an anti-tumor effect. In hepatocytes, SN-38 is glucuronidated by UDP-glucuronosyltransferase (UGT), to thereby form SN-38 glucuronate conjugate (SN-38G) having no cytotoxicity. SN-38G is excreted mainly to bile and then transferred to the intestinal tract, and finally excreted to feces. A portion of SN-38G excreted to the intestinal tract is deconjugated by β-glucuronidase of enteric bacteria, to thereby form active SN-38 again. The thus-formed free SN-38 is metabolized and excreted via the steps of re-absorption by the mediation of a transporter present at the intestinal tract epithelium, enterohepatic circulation, glucuronate conjugation by UGT in intestinal epithelial cells, and the like (Non-Patent Document 7). In the course of this metabolism, SN-38 damages the intestinal mucosa, to thereby possibly induce diarrhea. Also, some studies revealed that SN-38 adversely affects bone marrow, where cell division actively occurs, to thereby induce erythrocytopenia, leukocytopenia, and thrombocytopenia.

One cause for adverse events such as severe diarrhea and neutropenia was confirmed to be a change in exposure amount of SN-38 in the body caused by genetic polymorphism of UGT1A1. However, regarding therapeutic effects, there has not been reported that the therapeutic effect can be predicted by pharmacokinetics, due to the complex disposition, which include conversion of CPT-11 (pro-drug) to SN-38 (active metabolite) and its detoxication; re-generation of SN-38 in the course of enterohepatic circulation; and metabolism of CPT-11 and formation of SN-38 from the metabolite thereof, and due to antitumor effect generally determined by the tumor-related factors. Meanwhile, it has been reported that the carboxyl esterase mRNA expression amount in peripheral mononuclear cells correlates with the AUC ratio of SN-38 to SN-38G but does not correlate with the tumor reduction effect (Non-Patent Document 8).

There have also been reported the following tumor-related factors relating to the sensitivity or resistance to CPT-11: mutation of topoisomerase I, which is a target of SN-38, and expression amount thereof; activity of carboxyl esterase, the enzyme being involved in transformation of CPT-11 to SN-38 (Non-Patent Document 9); and transporters (multidrug resistance protein (MRP)-1, MRP-2, and breast cancer resistant protein (BCRP)/ABCG2), which affect the intracellular accumulation of CPT-11 and SN-38. Studies have also been conducted on correlations of cell proliferation antigen Ki-67, tumor suppressor gene p53, etc. with response to CPT-11 therapy. Quite recently, in vitro, studies have been conducted to predict sensitivity to an anticancer agent systematically through combination of anti-cancer agent sensitivity data with microarray analysis data, and for camptothecin derivatives, topotecan has been studied (Non-Patent Document 10). Also, a clinical study have revealed that the plasma TIMP-1 level, TIMP-1 being a tissue inhibitor of metalloproteinase-1 having anti-apoptosis action, is significantly correlated with the clinical prognosis of a metastatic colorectal cancer patient having undergone CPT-11 +5-FU combination therapy (Non-Patent Document 11). As described above, many studies have been conducted on sensitivity (to CPT-11) predicting bio-markers due to their necessity. However, a study has revealed that neither topoisomerase I (target) nor thymidylate synthase (possible 5-FU-sensitivity predictive factor) has clear correlation with therapeutic response in 5-FU+CPT-11 combination therapy (Non-Patent Document 12). Therefore, no definite bio-marker capable of predicting therapeutic response has been established.

PRIOR ART DOCUMENTS

Non-Patent Documents

Non-patent Document 1: J. Clin. Oncol. 1993; 11: 909-913
Non-patent Document 2: Semin. Oncol. 1999; 26 (1 Suppl. 5): 6-12
Non-patent Document 3: Lancet 1998; 352: 1407-1412
Non-patent Document 4: Pro. ASCO 2005; Abstract #3506
Non-patent Document 5: N. Engl. J. Med. 2000; 343: 905-914
Non-patent Document 6: Lancet 2000; 355: 1041-1047
Non-patent Document 7: Cancer Res. 1991; 51: 4187-4191
Non-patent Document 8: Clin. Cancer Res. 2005; 11: 6901-6907
Non-patent Document 9: Pharmacogenet Genomics 2007; 17: 1-10
Non-patent Document 10: Nat. Med. 2006; 12: 1294-1300
Non-patent Document 11: Clin. Cancer Res. 2007; 13: 4117-4122
Non-patent Document 12: Int. J. Cancer 2004; 111: 252-258

SUMMARY OF THE INVENTION

Problems to be Solved by the Invention

An object of the present invention is to provide a marker for determining sensitivity of a patient to an anti-cancer agent, which marker can determine whether or not the patient has a therapeutic response to the anti-cancer agent. Another object is to provide novel cancer therapeutic means employing the marker.

Means for Solving the Problems

In order to attain the aforementioned objects, the present inventors have searched for a marker for determining sensitivity to an anti-cancer agent by culturing human cancer cells, and comprehensively analyzing the intracellular metabolism behavior after exposure to SN-38 by means of a capillary electrophoresis/time-of-flight mass spectrometer (CE-TOFMS). As a result, the inventors have found substances which exhibit, after exposure to SN-38, a considerable rise in intracellular level in SN-38-low-sensitivity cells or in SN-38-high-sensitivity cells. These substances are a substance or a fragment thereof detected as an anion at m/z of 149.05 to 149.06, a substance or a fragment thereof detected as an anion at m/z of 152.99 to 153.00, a substance or a fragment thereof detected as a cation at m/z of 724.34 to 724.35, the peaks being determined by means of a mass spectrometer, glycerol 3-phosphate, dihydrobiopterin ($BH_2$), γ-aminobutyric acid (GABA), lactic acid, and 2-methylbutyroylcarnitine. The inventors have also found that asparagine and aspartic acid exhibit, after exposure to SN-38, time-dependent intracellular level profiles which differ from that exhibited by the control group in SN-38-high-sensitivity cells or in SN-38-low-sensitivity cells, and that a value calculated by dividing the [asparagine/aspartic acid] ratio obtained after exposure to SN-38 by the [asparagine/aspartic acid] ratio obtained without exposure to SN-38 can serve as a marker for determining sensitivity to an anti-cancer agent. Furthermore, the present inventors have searched for a marker for determining sensitivity to an anti-cancer agent by culturing human cancer cells of eight cell lines, and analyzing the metabolites in the cells through CE-TOFMS. As a result, the inventors have found several metabolites whose intracellular levels increase as decrease in sensitivity to an anti-cancer agent. The metabolites are substances involved in a metabolic pathway of any of GABA, 1-methyladenosine, and glutathione (GSH). On the basis of these findings, the inventors have carried out further studies, and have found that whether or not a cancer of a target cancer patient has a sensitivity to an anti-cancer agent can be determined through employing the levels of any of the metabolites in a biological sample derived from the cancer patient or the aforementioned metabolite level ratio as an index; that screening of an anti-cancer agent sensitivity enhancer can be accomplished through employment of the levels or variation in level of any of the metabolites or the aforementioned metabolite level ratio as an index; and that the therapeutic effect of the relevant anti-cancer agent can be drastically enhanced by use, in combination, of the anti-cancer agent sensitivity enhancer and the anti-cancer agent which is a sensitivity enhancement target of the enhancer. The present invention has been accomplished on the basis of these findings.

Accordingly, the present invention provides a marker for determining sensitivity to an anti-cancer agent, the marker comprising one or more substances selected from the group consisting of a substance or a fragment thereof detected as an anion at m/z of 149.05 to 149.06 (hereinafter may be referred to as metabolite A), a substance or a fragment thereof detected as an anion at m/z of 152.99 to 153.00 (hereinafter may be referred to as metabolite B), a substance or a fragment thereof detected as a cation at m/z of 724.34 to 724.35 (hereinafter may be referred to as metabolite D), the peaks being determined by means of a mass spectrometer, glycerol 3-phosphate, dihydrobiopterin, GABA, lactic acid, asparagine, aspartic acid, 2-methylbutyroylcarnitine, 1-methyladenosine, glutathione, and a substance involved in a metabolic pathway of any of these substances.

The present invention also provides a method for determining sensitivity of a subject to an anti-cancer agent, the method comprising measuring the level of any of these substances in a specimen derived from the subject.

The present invention also provides a kit for carrying out the method for determining sensitivity of a subject to an anti-cancer agent, the kit comprising a protocol for measuring the level of any of these substances in a specimen derived from the subject.

The present invention also provides a screening method for an anti-cancer agent sensitivity enhancer, the method comprising employing variation in expression of any of these substances as an index.

The present invention also provides an anti-cancer agent sensitivity enhancer obtained through the screening method.

The present invention also provides a composition for cancer therapy comprising, in combination, the anti-cancer agent sensitivity enhancer and an anti-cancer agent which is a sensitivity enhancement target of the enhancer.

The present invention also provides the above substances for use in determining the anti-cancer agent sensitivity.

Effects of the Invention

According to the marker for determining sensitivity to anti-cancer agent of the present invention, the therapeutic response of a patient to an anti-cancer agent can be appropriately determined before the therapy or in an early stage after start of the therapy. As a result, an anti-cancer agent having higher therapeutic effect can be selected, and progression of cancer and aggravation of adverse events, which would otherwise result from continuous administration of an anti-cancer agent exerting no expected therapeutic effect, can be prevented. Thus, reductions can be expected in the burden on patients and medical cost. In addition, when the marker of the present invention is used, a drug which can promote anti-cancer agent sensitivity can be selected through screening. Thus, through employment, in combination, of the target anti-cancer agent and an anti-cancer agent sensitivity enhancer to the anti-cancer agent, the expected cancer therapeutic effect can be drastically enhanced. The assay reagent for measuring the maker for determining sensitivity to an anti-cancer agent of the present invention is useful as an reagent for determining sensitivity to an anti-cancer agent.

BRIEF DESCRIPTION OF THE DRAWINGS

FIG. [1] A graph showing the time-dependent profile of average survival (%) of HT-29 cells and that of HCT-116 cells under exposure to 50 nmol/L SN-38.

FIG. [2] A graph showing the time-dependent profile of intracellular metabolite A level of HT-29 cells and that of HCT-116 cells under exposure to SN-38.

Figure 1:
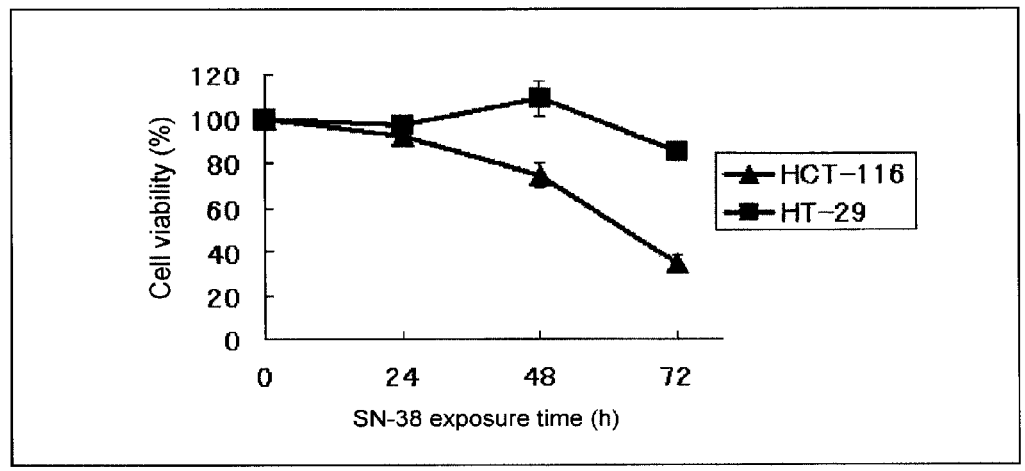
Figure 2:
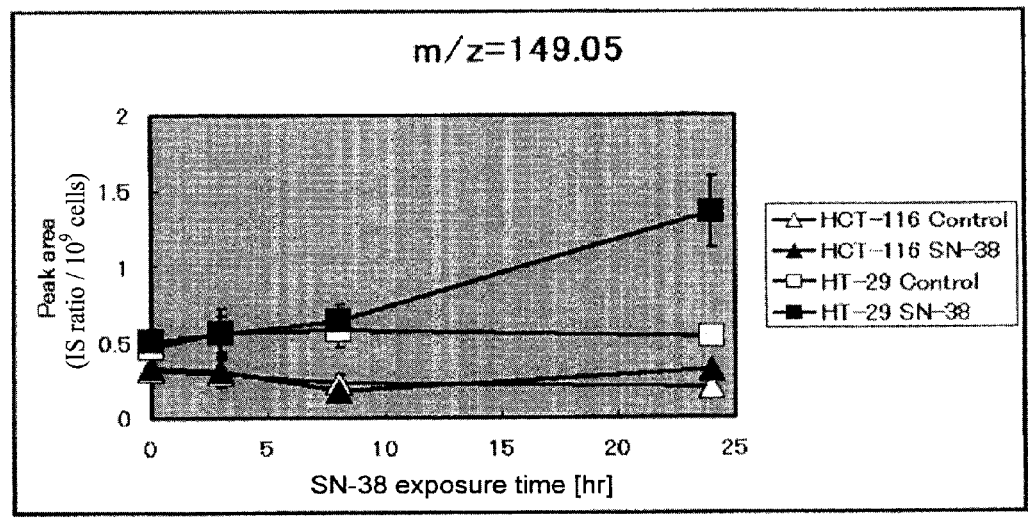
Figure 3:
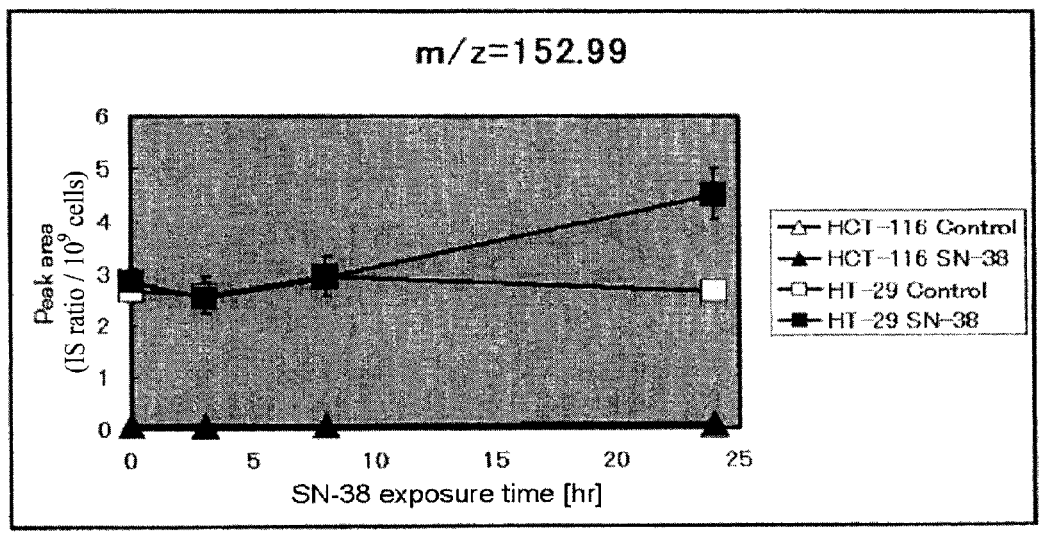
Figure 4:
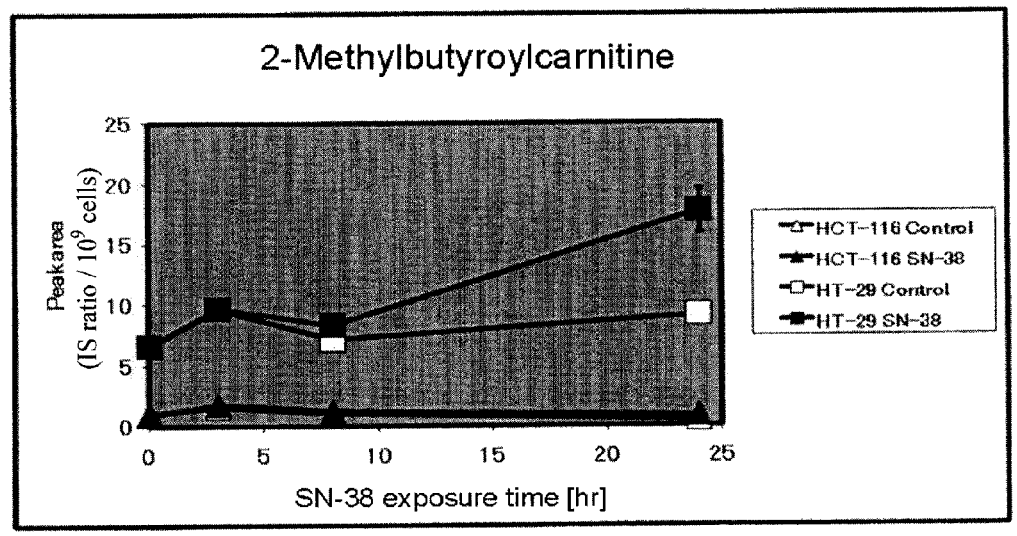
Figure 5:
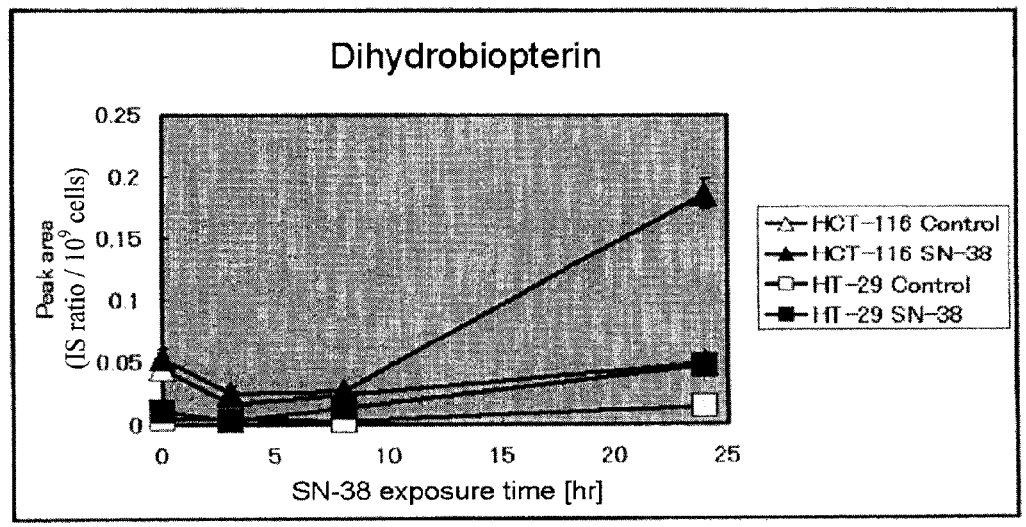
Figure 6:
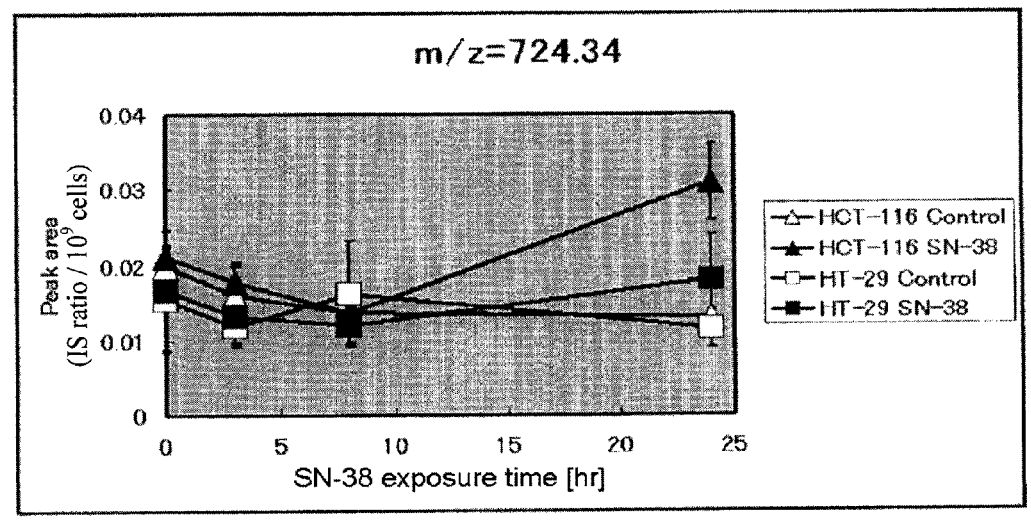
Figure 7:
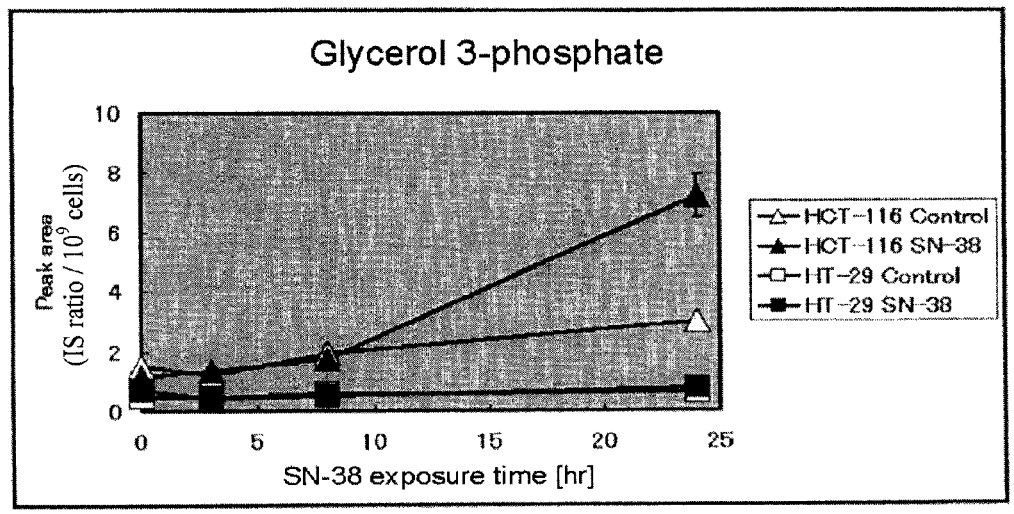

FIG. [3] A graph showing the time-dependent profile of intracellular metabolite B level of HT-29 cells and that of HCT-116 cells under exposure to SN-38.

FIG. [4] A graph showing the time-dependent profile of intracellular 2-methylbutyroylcarnitine level of HT-29 cells and that of HCT-116 cells under exposure to SN-38.

FIG. [5] A graph showing the time-dependent profile of intracellular $BH_2$ level of HT-29 cells and that of HCT-116 cells under exposure to SN-38.

FIG. [6] A graph showing the time-dependent profile of intracellular metabolite D level of HT-29 cells and that of HCT-116 cells under exposure to SN-38.

FIG. [7] A graph showing the time-dependent profile of intracellular glycerol 3-phosphate level of HT-29 cells and that of HCT-116 cells under exposure to SN-38.

FIG. [8] A graph showing the time-dependent profile of intracellular GABA level of HT-29 cells and that of HCT-116 cells under exposure to SN-38.

FIG. [9] A graph showing the time-dependent profile of intracellular lactic acid level of HT-29 cells and that of HCT-116 cells under exposure to SN-38.

FIG. [10] A graph showing the time-dependent profile of intracellular asparagine level of HT-29 cells and that of HCT-116 cells under exposure to SN-38.

FIG. [11] A graph showing the time-dependent profile of intracellular aspartic acid level of HT-29 cells and that of HCT-116 cells under exposure to SN-38.

FIG. [12] A graph showing the time-dependent profile of a value: [asparagine/aspartic acid]$_{SN-38}$/[asparagine/aspartic acid]$_{Control}$ (i.e., a value calculated by dividing the [asparagine/aspartic acid] ratio obtained after exposure to SN-38 by the [asparagine/aspartic acid] ratio obtained without exposure to SN-38) of HT-29 cells and that of HCT-116 cells.

FIG. [13] A graph showing the relationship between intracellular GABA levels in a steady state and sensitivity of cancer cell lines to SN-38.

FIG. [14] A table showing sensitivity of eight human colorectal cancer cell lines to SN-38.

FIG. [15] A graph showing the relationship between intracellular 1-methyladenosine levels in a steady state and sensitivity of cancer cell lines to SN-38, a graph showing the relationship between intracellular GABA levels in a steady state and sensitivity of cancer cell lines to SN-38, a graph showing the relationship between intracellular hypotaurine levels in a steady state and sensitivity of cancer cell lines to SN-38, a graph showing the relationship between intracellular glutathione levels in a steady state and sensitivity of cancer cell lines to SN-38, and a graph showing the relationship between intacellular 1-methylnicotinamide levels in a steady state and sensitivity of cancer cell lines to SN-38.

FIG. [16] Graphs showing the relationships between glutathione-metabolism-related substance intracellular levels in a steady state and sensitivity of cancer cell lines to SN-38.

MODES FOR CARRYING OUT THE INVENTION

The marker for determining sensitivity to an anti-cancer agent of the present invention is any substance selected from the group consisting of metabolites A, B, and D, glycerol 3-phosphate, dihydrobiopterin, GABA, lactic acid, asparagine, aspartic acid, 2-methylbutyroylcarnitine, 1-methyladenosine, glutathione, and a substance involved in a metabolic pathway of any of these substances (hereinafter may be referred to as "metabolism-related substance"). Among these substances, metabolites A, B, and D are a substance or a fragment thereof detected as an anion at m/z of 149.05 to 149.06, a substance or a fragment thereof detected as an anion at m/z of 152.99 to 153.00, and a substance or a fragment thereof detected as a cation at m/z of 724.34 to 724.35, respectively, the peaks being determined by means of a capillary electrophoresis/time-of-flight mass spectrometer (CE-TOFMS). These substances include all the substances that are involved in a metabolic pathway of any of these substances and that can vary the levels of these substances. Examples of such metabolism-related substances include a substance which promotes metabolism to these substances, a substance which inhibits the metabolism, a substance which promotes metabolism from these substances, and a substance which inhibits the metabolism.

One member of the marker for determining sensitivity to an anti-cancer agent of the present invention is glycerol 3-phosphate or a substance involved in a metabolic pathway thereof (hereinafter may be referred to as "glycerol 3-phosphate-metabolism-related substance"). Examples of the marker include glycerol 3-phosphate and all the substances that can vary the glycerol 3-phosphate level in a metabolic pathway thereof. Examples of such metabolism-related substances include a substance which promotes metabolism to glycerol 3-phosphate, a substance which inhibits the metabolism, a substance which promotes metabolism from glycerol 3-phosphate, and a substance which inhibits the metabolism. Of these, glycerol 3-phosphate is particularly preferred.

Another member of the marker for determining sensitivity to an anti-cancer agent of the present invention is dihydrobiopterin ($BH_2$) or a substance involved in a metabolic pathway thereof (hereinafter may be referred to as "$BH_2$-metabolism-related substance"). Examples of the marker include $BH_2$ and all the substances that can vary the $BH_2$ level in a metabolic pathway thereof. Examples of such metabolism-related substances include a substance which promotes metabolism to $BH_2$, a substance which inhibits the metabolism, a substance which promotes metabolism from $BH_2$, and a substance which inhibits the metabolism. Of these, $BH_2$ is particularly preferred.

Another member of the marker for determining sensitivity to an anti-cancer agent of the present invention is GABA or a substance involved in a metabolic pathway thereof (hereinafter may be referred to as "GABA-metabolism-related substance"). Examples of the marker include GABA and all the substances that can vary the GABA level in a metabolic pathway thereof. Examples of such metabolism-related substances include a substance which promotes metabolism to GABA, a substance which inhibits the metabolism, a substance which promotes metabolism from GABA, and a substance which inhibits the metabolism. Of these, GABA is particularly preferred.

Another member of the marker for determining sensitivity to an anti-cancer agent of the present invention is lactic acid or a substance involved in a metabolic pathway thereof (hereinafter may be referred to as "lactic acid-metabolism-related substance"). Examples of the marker include lactic acid and all the substances that can vary the lactic acid level in a metabolic pathway thereof. Examples of such metabolism-related substances include a substance which promotes metabolism to lactic acid, a substance which inhibits the metabolism, a substance which promotes metabolism from lactic acid, and a substance which inhibits the metabolism. Of these, lactic acid is particularly preferred.

Another member of the marker for determining sensitivity to an anti-cancer agent of the present invention is asparagine, aspartic acid, or a substance involved in a metabolic pathway thereof. In the case of asparagine and aspartic acid, the ratio therebetween is an important factor. Specifically, the ratio is the ratio [asparagine/aspartic acid] calculated from the asparagine level and the aspartic acid level, more specifically, the value calculated by dividing the [asparagine/aspartic acid] ratio obtained after exposure to an anti-cancer agent by the [asparagine/aspartic acid] ratio obtained without exposure the anti-cancer agent:

([asparagine/aspartic acid]$_{Anti\text{-}cancer\ agent}$/[asparagine/aspartic acid]$_{Control}$).

Examples of the substance which may be used for the above calculation include asparagine, aspartic acid, and a substance involved in a metabolic pathway of asparagine or aspartic acid (hereinafter may be referred to as "asparagine-metabolism-related substance" or "aspartic acid-metabolism-related substance"). Examples of the marker include all the substances that can vary the asparagine level or the aspartic acid level in a metabolic pathway thereof. Examples of such metabolism-related substances include a substance which promotes metabolism to asparagine or aspartic acid, a substance which inhibits the metabolism, a substance which promotes metabolism from asparagine or aspartic acid, and a substance which inhibits the metabolism. Of these, asparagine and aspartic acid are particularly preferred.

Another member of the marker for determining sensitivity to an anti-cancer agent of the present invention is 2-methylbutyroylcarnitine or a substance involved in a metabolic pathway thereof (hereinafter may be referred to as "2-methylbutyroylcarnitine-metabolism-related substance"). Examples of the marker include 2-methylbutyroylcarnitine and all the substances that can vary the 2-methylbutyroylcarnitine level in a metabolic pathway thereof. Examples of such metabolism-related substances include a substance which promotes metabolism to 2-methylbutyroylcarnitine, a substance which inhibits the metabolism, a substance which promotes metabolism from 2-methylbutyroylcarnitine, and a substance which inhibits the metabolism. Of these, 2-methylbutyroylcarnitine is particularly preferred.

Another member of the marker for determining sensitivity to an anti-cancer of the present invention is 1-methyladenosine or a substance involved in a metabolic pathway thereof (hereinafter may be referred to as "1-methyladenosine-metabolism-related substance"). Examples of the marker include 1-methyladenosine and all the substances that can vary the 1-methyladenosine level in a metabolic pathway thereof. Examples of such metabolism-related substances include a substance which promotes metabolism to 1-methyladenosine, a substance which inhibits the metabolism, a substance which promotes metabolism from 1-methyladenosine, and a substance which inhibits the metabolism. Of these, 1-methyladenosine is particularly preferred.

Another member of the marker for determining sensitivity to an anti-cancer agent of the present invention is glutathione or a substance involved in a metabolic pathway thereof (hereinafter may be referred to as "glutathione-metabolism-related substance"). Examples of the marker include glutathione and all the substances that can vary the glutathione level in a metabolic pathway thereof. Examples of such metabolism-related substances include a substance which promotes metabolism to glutathione, a substance which inhibits the metabolism, a substance which promotes metabolism from glutathione, and a substance which inhibits the metabolism. Of these, glutathione, hypotaurine, 1-methylnicotinamide, taurine, glutathione disulfide (GSSG), S-adenosyl homocysteine, nicotinamide, γ-glutamyl cysteine (γ-Glu-Cys), and spermine are preferred, with glutathione, hypotaurine, and -methylnicotinamide being particularly preferred.

As shown in the Examples described hereinbelow, the level of metabolite A, metabolite B, or 2-methylbutyroylcarnitine was found to considerably increase in HT-29 cells, which are low-sensitive to SN-38, after exposure to SN-38. In contrast, no significant variation in level was observed in HCT-116 cells, which are high-sensitive to SN-38. Therefore, these substances are useful as markers for determining sensitivity to an anti-cancer agent, particularly to CPT-11, SN-38, or the like.

As shown in the Examples described hereinbelow, the level of metabolite D, glycerol 3-phosphate, $BH_2$, or lactic acid was found to considerably increase in HCT-116 cells, which are high-sensitive to SN-38, after exposure to SN-38. In contrast, no significant variation in level was observed in HT-29 cells, which are low-sensitive to SN-38. Therefore, these substances are useful as markers for determining sensitivity to an anti-cancer agent, particularly to CPT-11, SN-38, or the like.

As shown in the Examples described hereinbelow, the GABA level was found to considerably increase in HT-29 cells, which are low-sensitive to SN-38, after exposure to SN-38. In contrast, no significant variation in level was observed in HCT-116 cells, which are high-sensitive to SN-38. The intrinsic metabolite level of GABA was high in HT-29 cells, which are low-sensitive to SN-38, and low in HCT-116 cells, which are high-sensitive to SN-38. Through further investigation with eight human cancer cell lines, the intracellular GABA level increased as the sensitivity to SN-38 decreased. Therefore, GABA is useful as a marker for determining sensitivity to an anti-cancer agent, particularly to CPT-11, SN-38, or the like.

As shown in the Examples described hereinbelow, the asparagine level profile in HCT-116 cells, which are high-sensitive to SN-38, after exposure to SN-38, was different from that exhibited by the control group. In contrast, no significant difference was observed in the profile in HT-29 cells, which are low-sensitive to SN-38, between the SN-38-exposure group and the control group. In addition, the aspartic acid level profile in HT-29 cells, which are low-sensitive to SN-38, after exposure to SN-38, was different from that exhibited by the control group. In contrast, no significant difference was observed in the profile in HCT-116 cells, which are high-sensitive to SN-38, between the SN-38-exposure group and the control group. The value calculated by dividing the [asparagine/aspartic acid] ratio obtained after exposure to SN-38 by the [asparagine/aspartic acid] ratio obtained without exposure thereto (i.e., [asparagine/aspartic acid]$_{SN\text{-}38}$/[asparagine/aspartic acid]$_{Control}$) considerably increased in HCT-116 cells, which are high-sensitive to SN-38, but considerably decreased in HT-29 cells, which are low-sensitive to SN-38. Therefore, the [asparagine/aspartic acid] ratio is useful as a marker for determining sensitivity to an anti-cancer agent, particularly to CPT-11, SN-38, or the like.

As shown in the Examples described hereinbelow, through further investigation with eight human cancer cell lines, the intracellular 1-methyladenosine level and the intracellular levels of glutathione-metabolism-related substances increased as the sensitivity to SN-38 decreased. Therefore, 1-methyladenosine and glutathione-metabolism-related substances are useful as markers for determining sensitivity to an anti-cancer agent, particularly to CPT-11, SN-38, or the like.

No particular limitation is imposed on the anti-cancer agent to which the marker for determining sensitivity to an anti-cancer agent of the present invention is applied. Examples of the anti-cancer agent include CPT-11, SN-38, oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab/ozogamicin, bortezomib, erlotinib, cetuximab, bevacizumab, sunitinib, sorafenib, dasatinib, panitumumab, asparaginase, tretinoin, arsenic trioxide, salts thereof, and active metabolites thereof. Among them, plant alkaloid-derived anti-cancer agents (e.g., CPT-11, SN-38, and salts thereof) are preferred.

In order to determine sensitivity of a subject to an anti-cancer agent by use of the marker for determining sensitivity to an anti-cancer agent of the present invention, the level of any of these metabolism-related substances in a specimen may be measured. Examples of the specimen include biological samples derived from subjects having cancer (i.e., cancer patients) such as blood, serum, plasma, urine, cancer tissue/cell, ascitic fluid, pleural fluid, cerebrospinal fluid, feces, and expectoration. Of these, serum is particularly preferred.

Examples of the target cancer of the present invention include lip, oral, pharyngeal cancers such as pharyngeal cancer; gastrointestinal cancers such as esophageal cancer, gastric cancer, and colorectal cancer; respiratory and intrathoracic organ cancers such as lung cancer; bone cancer and articular cartilage cancer; skin melanoma, squamous cell cancer, and other skin cancers; mesothelial and soft tissue cancers such as mesothelioma; female genital cancers such as breast cancer, uterine cancer, and ovarian cancer; male genital cancers such as prostate cancer; urinary tract cancers such as bladder cancer; eye, brain, and central nervous system cancers such as brain tumor; thyroid and other endocrine cancers; lymphoid tissue, hematopoietic tissue, and related tissue cancers such as non-Hodgkin's lymphoma and lymphoid leukemia; and metastatic cancers from these cancers as primary lesions. The present invention is particularly preferably applied to non-small-cell lung cancer, small-cell lung cancer, cervical cancer, ovarian cancer, gastric cancer, colorectal cancer, squamous cell cancer, and malignant lymphoma.

The means for measuring these metabolism-related substances in a specimen may be selected in accordance with the substance to be measured. Examples of the means include mass spectrometers (e.g., CE-TOFMS and gas chromatography-mass spectrometry (GC-MS)), HPLC, immunological assay, and biological assay.

In the case where metabolite A, metabolite B, or 2-methylbutyroylcarnitine is employed with respect to a target anti-cancer agent, the sensitivity of the target cancer to the anti-cancer agent is determined as follows. The level of any of these metabolism-related substances in a biological sample derived from a cancer patient is measured before and after administration of the anti-cancer agent. When the metabolism-related substance level increases after administration of the anti-cancer agent, the cancer is determined to have no sensitivity to the anti-cancer agent, whereas when the substance level is constant after administration of the anti-cancer agent, the cancer is determined to have sensitivity to the anti-cancer agent.

Alternatively, when the level of any of the metabolism-related substances is higher than a predetermined standard level of the substance in an early stage after administration of the anti-cancer agent, the cancer can be determined to have no sensitivity to the anti-cancer agent. When the cancer has no sensitivity to the anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events which would otherwise be caused by continuous administration of an ineffective anti-cancer agent.

In the case where metabolite D, glycerol 3-phosphate, $BH_2$, or lactic acid is employed with respect to a target anti-cancer agent, the sensitivity of the target cancer to the anti-cancer agent is determined as follows. The level of any of these metabolism-related substances in a biological sample derived from a cancer patient is measured before and after administration of the anti-cancer agent. When the metabolism-related substance level increases after administration of the anti-cancer agent, the cancer is determined to have sensitivity to the anti-cancer agent, whereas when the substance level is constant after administration of the anti-cancer agent, the cancer is determined to have no sensitivity to the anti-cancer agent.

Alternatively, when the level of any of the metabolism-related substances is lower than a predetermined standard level of the substance in an early stage after administration of the anti-cancer agent, the cancer can be determined to have no sensitivity to the anti-cancer agent. When the cancer has no sensitivity to the anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events which would otherwise be caused by continuous administration of an ineffective anti-cancer agent.

In the case where GABA is employed with respect to a target anti-cancer agent, the sensitivity of the target cancer to the anti-cancer agent is determined as follows. The level of any of the metabolism-related substances in a biological sample derived from a cancer patient is measured before and after administration of the anti-cancer agent. When the metabolism-related substance level increases after administration of the anti-cancer agent, the cancer is determined to have no sensitivity to the anti-cancer agent, whereas when the substance level is constant after administration of the anti-cancer agent, the cancer is determined to have sensitivity to the anti-cancer agent.

Alternatively, when the level of any of the metabolism-related substances is higher than a predetermined standard level of the substance in an early stage after administration of the anti-cancer agent, the cancer can be determined to have no sensitivity to the anti-cancer agent. When the cancer has no sensitivity to the anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events which would otherwise be caused by continuous administration of an ineffective anti-cancer agent.

In the case where the [asparagine/aspartic acid] ratio is employed with respect to a target anti-cancer agent, the sensitivity of the target cancer to the anti-cancer agent is determined as follows. The asparagine level and the aspartic acid level in a biological sample derived from a cancer patient are measured before and after administration of the anti-cancer agent. When the [asparagine/aspartic acid] ratio obtained from the measurements increases after administration of the anti-cancer agent, the cancer is determined to have sensitivity to the anti-cancer agent, whereas when the [asparagine/aspartic acid] ratio decreases after administration of the anti-cancer agent, the cancer is determined to have no sensitivity to the anti-cancer agent.

Alternatively, when the [asparagine/aspartic acid] ratio is lower than a predetermined standard level in an early stage after administration of the anti-cancer agent, the cancer can be determined to have no sensitivity to the anti-cancer agent. When the cancer has no sensitivity to the anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events which would otherwise be caused by continuous administration of an ineffective anti-cancer agent.

In the case where 1-methyladenosine or a glutathione-metabolism-related substance is employed with respect to a target anti-cancer agent, the sensitivity of the target cancer to the anti-cancer agent is determined as follows. When the level of any of the metabolism-related substances is higher than a predetermined standard level of the substance before administration of the anti-cancer agent, the cancer can be determined to have no sensitivity to the anti-cancer agent. When the cancer has no sensitivity to the anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events which would otherwise be caused by continuous administration of an ineffective anti-cancer agent.

In order to carry out the method of the present invention for determining sensitivity of a subject to an anti-cancer agent, preferably, a kit containing a protocol for measuring the level of any of the metabolism-related substances in a specimen is employed. The kit contains a reagent for measuring any of these metabolism-related substances, an indication of an instruction manual for use of the reagent, standards for determining the presence or absence of sensitivity to the anti-cancer agent, etc. The standards include standard levels of these metabolism-related substances, a standard ratio, a high threshold level, a high threshold ratio, a low threshold level, a low threshold ratio, factors affecting the measurements, the degree of the effects, etc. These levels may be set so as to suit the target anti-cancer agent selected. The sensitivity determination may be performed as described above on the basis of the standards.

In the case of metabolite A, metabolite B, 2-methylbutyroylcarnitine, GABA, 1-methyladenosine, or a glutathione-metabolism-related substance, screening of an anti-cancer agent sensitivity enhancer can be performed through employment, as an index, of variation in expression of any of the substances, specifically suppression of variation or decrease in level. That is, a substance which lowers the level of metabolite A, metabolite B, 2-methylbutyroylcarnitine, GABA, 1-methyladenosine, or a glutathione-metabolism-related substance in vitro or in vivo before administration of the anti-cancer agent enhances sensitivity to an anti-cancer agent, or which suppresses variation or lowers the level enhances the sensitivity to the anti-cancer agent. For example, in an in vitro case, a substance which lowers the level of metabolite A, metabolite B, 2-methylbutyroylcarnitine, GABA, 1-methyladenosine, or a glutathione-metabolism-related substance of various cancer cells before exposure to an anti-cancer agent, the cancer cells treated with the substance in advance, is a substance which enhances the sensitivity to the anti-cancer agent (i.e., anti-cancer agent sensitivity enhancer). Also, in an in vitro case, a substance which suppresses variation in level of metabolite A, metabolite B, 2-methylbutyroylcarnitine, GABA, 1-methyladenosine, or a glutathione-metabolism-related substance of various cancer cells after exposure to an anti-cancer agent is a substance which enhances the sensitivity to the anti-cancer agent (i.e., anti-cancer agent sensitivity enhancer). Also, in an in vivo case, a substance which lowers the level of metabolite A, metabolite B, 2-methylbutyroylcarnitine, GABA, 1-methyladenosine, or a glutathione-metabolism-related substance in a cancer-bearing animal before exposure to an anti-cancer agent, or a substance which suppresses variation in level of the same or lowers the level of the same after exposure to the anti-cancer agent is a substance which enhances the sensitivity to the anti-cancer agent (i.e., anti-cancer agent sensitivity enhancer).

In the case of metabolite D, glycerol 3-phosphate, $BH_2$, or lactic acid, screening of an anti-cancer agent sensitivity enhancer can be performed through employment, as an index, of variation in expression of any of the substances, specifically promotion of variation or increase in level. That is, a substance which promotes variation in level of metabolite D, glycerol 3-phosphate, $BH_2$, or lactic acid or which increases the level of the same, in vitro or in vivo after exposure to the anti-cancer agent enhances the sensitivity to the anti-cancer agent. For example, in an in vitro case, a substance which promotes variation in level of metabolite D, glycerol 3-phosphate, $BH_2$, or lactic acid in various cancer cells after exposure to an anti-cancer agent is a substance which enhances the sensitivity to the anti-cancer agent (i.e., anti-cancer agent sensitivity enhancer). Also, in an in vivo case, a substance which promotes variation in level of metabolite D, glycerol 3-phosphate, $BH_2$, or lactic acid in a cancer-bearing animal or a substance which increases the level of the same, after exposure to an anti-cancer agent is a substance which enhances the sensitivity to the anti-cancer agent (i.e., anti-cancer agent sensitivity enhancer).

Alternatively, screening of an anti-cancer agent sensitivity enhancer can be performed through employment, as an index, of variation in [asparagine/aspartic acid] ratio after exposure to an anti-cancer agent, specifically an increase in [asparagine/aspartic acid] ratio. That is, a substance which increases the [asparagine/aspartic acid] ratio in vitro or in vivo after exposure to the anti-cancer agent enhances the sensitivity to the anti-cancer agent. For example, in an in vitro case, a substance which increases the [asparagine/aspartic acid] ratio in various cancer cells after exposure to an anti-cancer agent is a substance which enhances the sensitivity to the anti-cancer agent (i.e., anti-cancer agent sensitivity enhancer). Also, in an in vivo case, a substance which increases the [asparagine/aspartic acid] ratio in a cancer-bearing animal after exposure to an anti-cancer agent is a substance which enhances the sensitivity to the anti-cancer agent (i.e., anti-cancer agent sensitivity enhancer). Notably, the [asparagine/aspartic acid] ratio may be replaced by the value calculated by dividing the [asparagine/aspartic acid] ratio obtained after exposure to an anti-cancer agent by the [asparagine/aspartic acid] ratio obtained without exposure thereto. Through employment of the calculated value, screening of an anti-cancer agent sensitivity enhancer can be performed sharply at higher sensitivity.

Screening of an anti-cancer agent can be performed through employment, as an index, of the level of metabolite A, metabolite B, 2-methylbutyroylcarnitine, GABA, 1-methyladenosine, or a glutathione-metabolism-related substance. That is, a substance which can vary the level of any of these metabolism-related substances in vitro or in vivo is an anti-cancer agent. For example, in an in vitro case, a substance which varies the level of metabolite A, metabolite B, 2-methylbutyroylcarnitine, GABA, 1-methyladenosine, or a glutathione-metabolism-related substance in various cancer cells after exposure to the substance can serve as an anti-cancer agent. Also, when the level of any of these metabolism-related substances in a cancer-bearing animal varies after administration of a substance thereto, the substance can serve as an anti-cancer agent. If the anti-cancer agent is expected to exhibit a pharmaceutical effect, the variation in metabolism-related substance level is observed before reduction in the size of tumor or a cell-killing effect. Therefore, screening based on the metabolism-related substance level as an index can realize, for a shorter period of time, determination whether or not the test substance serves as a useful anti-cancer agent, whereby efforts and cost involved in the development of anti-cancer agents are greatly expected to be reduced.

Screening of an anti-cancer agent can be performed through employment, as an index, of the level of metabolite D, glycerol 3-phosphate, $BH_2$, or lactic acid. That is, a substance which can increase the level of any of these metabolism-related substances in vitro or in vivo is an anti-cancer agent. For example, in an in vitro case, a substance which increases the level of metabolite D, glycerol 3-phosphate, $BH_2$, or a lactic acid-metabolism-related substance in various cancer cells after exposure to the substance can serve as an anti-cancer agent. Also, when the level of any of these metabolism-related substances in a cancer-bearing animal increases after administration of a substance thereto, the substance can serve as an anti-cancer agent. If the anti-cancer agent is expected to exhibit a pharmaceutical effect, the increase in metabolism-related substance level is observed before reduction in the size of tumor or a cell-killing effect. Therefore, screening based on the metabolism-related substance level as an index can realize, for a shorter period of time, determination whether or not the test substance serves as a useful anti-cancer agent, whereby efforts and cost involved in the development of anti-cancer agents are greatly expected to be reduced.

Screening of an anti-cancer agent can be performed through employment of the [asparagine/aspartic acid] ratio as an index. That is, a substance which can increase the [asparagine/aspartic acid] ratio in vitro or in vivo is an anti-cancer agent. For example, in an in vitro case, a substance which increases the [asparagine/aspartic acid] ratio in various cancer cells after exposure to the substance can serve as an anti-cancer agent. Also, when the [asparagine/aspartic acid] ratio in a cancer-bearing animal increases after administration of a substance thereto, the substance can serve as an anti-cancer agent. If the anti-cancer agent is expected to exhibit a pharmaceutical effect, the increase in [asparagine/aspartic acid] ratio is observed before reduction in the size of tumor or a cell-killing effect. Therefore, screening based on the [asparagine/aspartic acid] ratio as an index can realize, for a shorter period of time, determination whether or not the test substance serves as a useful anti-cancer agent, whereby efforts and cost involved in the development of anti-cancer agents are greatly expected to be reduced.

Notably, the [asparagine/aspartic acid] ratio may be replaced by the value calculated by dividing the [asparagine/aspartic acid] ratio obtained after exposure to a test substance by the [asparagine/aspartic acid] ratio obtained without exposure thereto. Through employment of the calculated value, screening of an anti-cancer agent can be performed sharply at higher sensitivity.

Through employment, in combination, of the thus-obtained anti-cancer agent sensitivity enhancer and an anti-cancer agent which is a sensitivity enhancement target of the enhancer, the therapeutic effect of the anti-cancer agent is drastically enhanced. The combination of the anti-cancer agent sensitivity enhancer and the anti-cancer agent which is a sensitivity enhancement target of the enhancer may be a composition containing both ingredients, or a combined drug of preparations containing individual ingredients. These two ingredients may be administered through different routes. The target anti-cancer agents which may be employed here are the same as described above. Examples of the anti-cancer agent include CPT-11, SN-38, oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab/ozogamicin, bortezomib, erlotinib, cetuximab, bevacizumab, sunitinib, sorafenib, dasatinib, panitumumab, asparaginase, tretinoin, arsenic trioxide, salts thereof, and active metabolites thereof.

Among them, plant alkaloid-derived anti-cancer agents (e.g., CPT-11, SN-38, and salts thereof) are preferred.

EXAMPLES

The present invention will next be described in more detail by way of examples.

Example 1

(1) Method
(a) Cells Employed

Two human colorectal cancer cell lines (HCT-116 and HT-29) employed were obtained from Kabushiki Kaisha Yakult Honsha.

Cell culturing was performed by means of a φ100 mm/Tissue Culture Dish (IWAKI) with a medium (Doulbecco's modified Eagle's Medium, 10% fetal bovine serum) at 37° C. under 5% $CO_2$.

(b) Drugs

SN-38 powder was obtained from Kabushiki Kaisha Yakult Honsha. SN-38 was dissolved in DMSO, and, before use, the solution was diluted so that the DMSO concentration of each of the culture media employed in experiments was adjusted to 0.1% or less.

(c) Evaluation of Sensitivity of Cancer to SN-38

Cells of two colorectal cancer cell lines (HCT-116 and HT-29) were exposed to 50 nmol/L SN-38, and 24, 48, and 72 hours after drug exposure, cell viability was determined by means of an MTS assay (CellTiter96™AQ$_{ueous}$ One Solution Cell Proliferation Assay, Promega). Sensitivity evaluation of each cell line was performed in triplicate with three different passage numbers of cells, and the mean value and standard deviation were calculated.

(d) Exposure to SN-38 and Recovery of Metabolites in the Cells

Cells of two colorectal cancer cell lines (HCT-116 and HT-29) were exposed to SN-38 by changing the culture medium to a medium containing SN-38 at 50 nmol/L. The same culture was performed in an SN-38-free medium (control group). After exposure to SN-38 (0 hr, 3 hr, 8 hr, and 24 hr), the cells were washed on ice with 5% mannitol (4° C.). Immediately thereafter, methanol (4° C., containing an internal standard) was added to the washed cells, to thereby inactivate present enzymes, and stored at −80° C. Separately, cells for cell count were provided in addition to the cells from which metabolites were extracted, and subjected to the above treatment and cell counting. The data were employed in correction of the cell counts.

(e) Preparation of Metabolome Sample

Chloroform and Milli-Q water were added to the methanol solution stored at −80° C., and liquid-liquid extraction was performed, to thereby removed contaminants. A water-methanol layer containing metabolites was recovered and centrifugally filtered through an ultrafilter with a molecular weight cutoff of 5,000 Da, to thereby remove proteins. The filtrate was dried under reduced pressure and then stored at −80° C. The filtrate was dissolved in Milli-Q water immediately before the measurement and then subjected to metabolome measurement.

(f) Metabolome Measurement

Comprehensive analysis of intracellular metabolites was performed by means of a capillary electrophoresis-time-of-flight-type mass spectrometer (CE-TOFMS) (product of Agilent Technologies). In the comprehensive analysis of cationic metabolites, voltage was applied so that the outlet of the capillary served as a negative electrode, whereas in the comprehensive analysis of anionic metabolites, voltage was applied so that the outlet of the capillary served as a positive electrode. Metabolites detected at m/z values of 50 to 1,000 were simultaneously quantitated.

(2) Results

The time-dependent profile of cell viability after exposure to 50 nmol/L SN-38 was investigated through the MTS assay. The viabilities of the two cell lines after exposure for 24 hours were almost the same. However, as the exposure time was prolonged, the viability of each cell line decreased, and the difference increased as elapse of time. After exposure for 72 hours, the viabilities were found to be about 85% (HT-29) and about 35% (HCT-116), indicating that the sensitivity of HT-29 to SN-38 was lower than that of HCT-116 (FIG. 1).

Intracellular metabolome variation attributed to exposure to SN-38 was comprehensively analyzed through a comprehensive metabolome analysis technique employing CE-TOFMS. In the case of each cell line, the SN-38 24 hour exposure group was compared with the control group, and peaks having an intensity in the exposure group considerably different from that in the control group were selected. The time-dependent profiles (after exposure to SN-38) of the thus-selected peaks were visualized as graphs, whereby the following metabolites exhibiting characteristic variation were found (FIGS. 2 to 7, and 9 to 11).

(1) Metabolites exhibiting a considerable increase in intracellular level in HT-29 after exposure to SN-38
  m/z=149.05 to 149.06 (anion)
  m/z=152.99 to 153.00 (anion)
  m/z=246.16 to 246.17 (cation)
(2) Metabolites exhibiting a considerable increase in intracellular level in HCT-116 after exposure to SN-38
  m/z=171.00 (anion)
  m/z=240.10 to 240.11 (cation)
  m/z=724.34 to 724.35 (cation)
  m/z=89.02 (anion)
(3) Peak at which an intracellular level variation profile of the SN-38 exposure group differing from that of the control group was observed in HCT-116
  m/z=133.06 (cation)
(4) Peak at which an intracellular level variation profile of the SN-38 exposure group differing from that of the control group was observed in HT-29
  m/z=134.04 (cation)

The composition of the substance detected as a peak at m/z of 171.00 was estimated by use of analysis software Analyst™ QS (Applied Biosystems, Inc.). From the data including the isotope ratio to a parent peak and precise mass, the composition of the substance detected at m/z of 171.00 was determined to be $C_3H_8O_6P$ (as ion). By use of KEGG PATHWAY (life system information integrated database (http://www.kegg.jp/) produced by Kyoto University, a substance assumed by the ion composition was retrieved. As a result, the peak was found to be attributed to glycerol 3-phosphate. Through investigation by use of a standard sample of glycerol 3-phosphate, the observed migration time in capillary electrophoresis was found to coincide with that of the standard sample.

The composition of the substance detected as a peak at m/z of 149.05 to 149.06 (anion) was estimated through capillary electrophoresis-quadrupole time-of-flight mass spectrometry (CE-QTOFMS). As a result, the composition of the substance detected at m/z of 149.05 to 149.06 was estimated to be $C_5H_9O_5$ (as ion).

The composition of the substance detected as a peak at m/z of 152.99 to 153.00 (anion) was estimated through CE-QTOFMS. As a result, the composition of the substance detected at m/z of 152.99 to 153.00 was estimated to be $C_3H_6O_5P$ (as ion).

The composition of the substance detected as a peak at m/z of 246.16 to 246.17 (cation) was estimated through CE-QTOFMS. As a result, the composition of the substance detected at m/z of 246.16 to 246.17 was determined to be $C_{12}H_{24}NO_4$ (as ion). By use of Human Metabolome Database (http://www.hmdb.ca/), a substance assumed by the ion composition was retrieved. As a result, the peak was found to be attributed to 2-methylbutyroylcarnitine. Through investigation by use of a standard sample of 2-methylbutyroylcarnitine, the observed migration time in capillary electrophoresis was found to coincide with that of the standard sample.

The composition of the substance detected as a peak at m/z of 240.10 to 240.11 (cation) was estimated through CE-QTOFMS. As a result, the composition of the substance detected at m/z of 240.10 to 240.11 (cation) was determined to be $C_9H_{14}N_5O_3$ (as ion). By use of Human Metabolome Database (http://www.hmdb.ca/), a substance assumed by the ion composition was retrieved. As a result, the peak was found to be attributed to dihydrobiopterin. Through investigation by use of a standard sample of dihydrobiopterin, the observed migration time in capillary electrophoresis was found to coincide with that of the standard sample.

The composition of the substance detected as a peak at m/z of 89.02 was estimated by use of analysis software Analyst™ QS (Applied Biosystems, Inc.). From the data including the isotope ratio to a parent peak and precise mass, the composition of the substance detected at m/z of 89.02 was determined to be $C_3H_5O_3$ (as ion). By use of KEGG PATHWAY (life system information integrated database (http://www.kegg.jp/) produced by Kyoto University, a substance assumed by the ion composition was retrieved. As a result, the peak was found to be attributed to lactic acid. Through investigation by use of a standard sample of lactic acid, the observed migration time in capillary electrophoresis was found to coincide with that of the standard sample.

Figure 8:
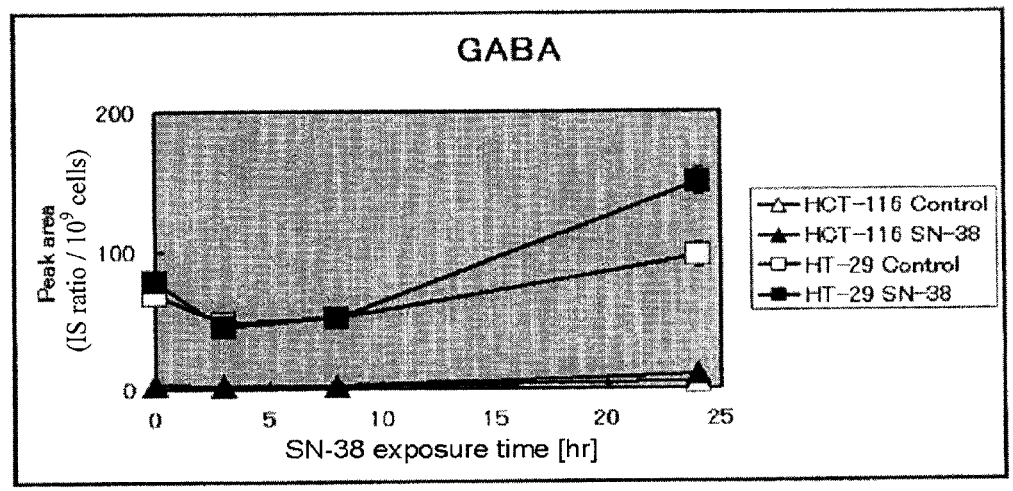
Figure 9:
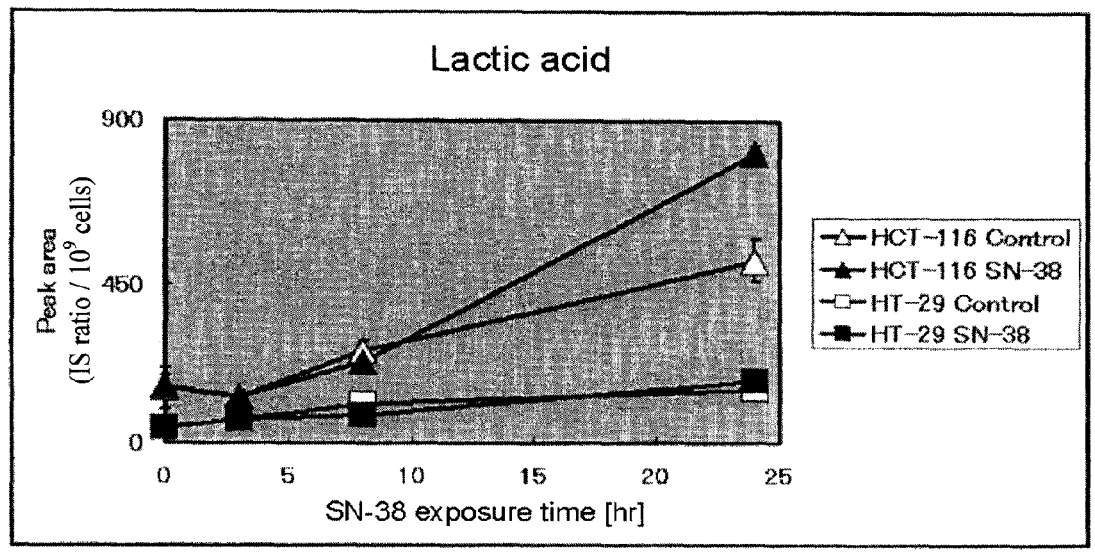
Figure 10:
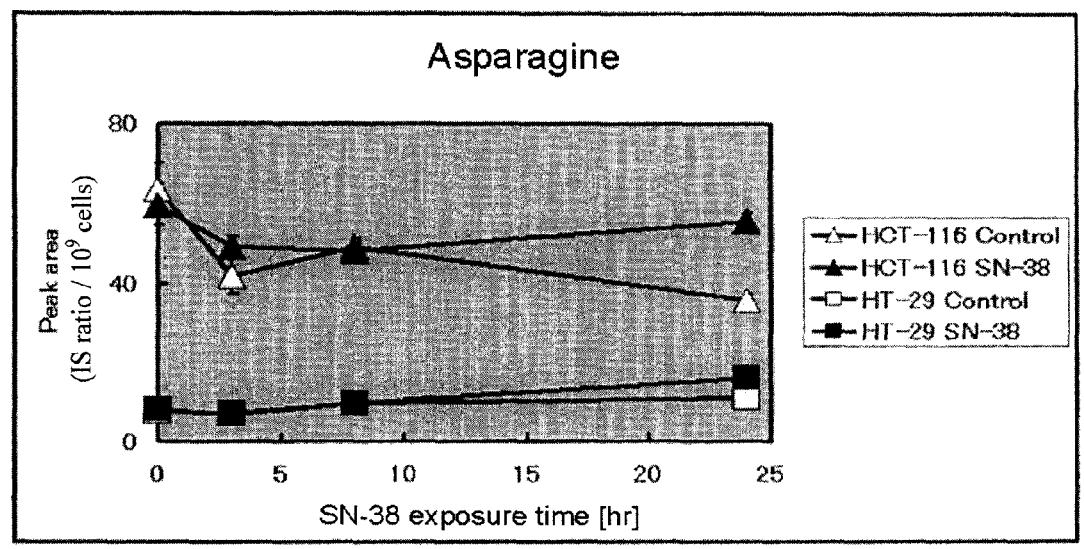
Figure 11:
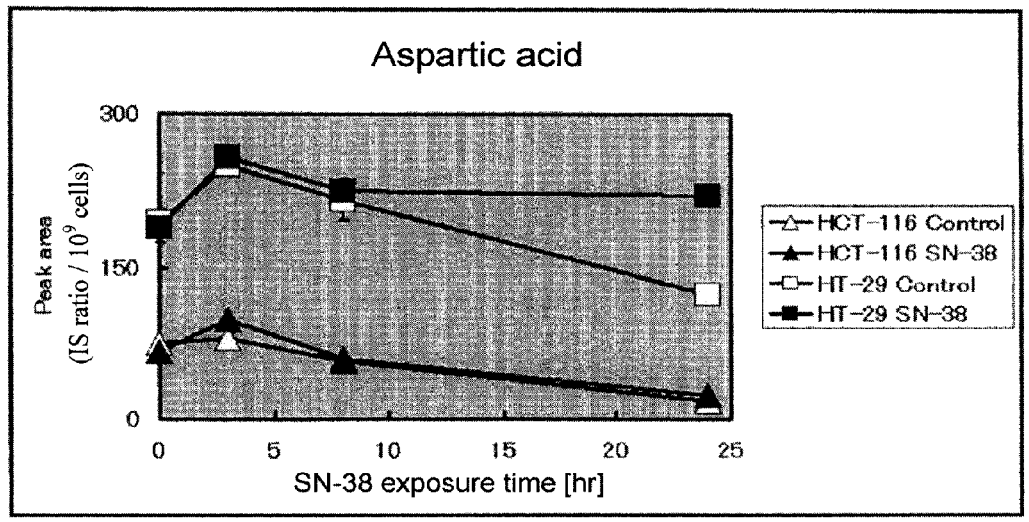

The control groups of each cell line were compared, and peaks having an intensity in one control group considerably different from that in the other control group were selected. Among the thus-selected peaks, a substance detected as a peak at m/z of 104.070 exhibited high intracellular level in HT-29 (SN-38-low-sensitivity cells) and low intracellular level in HCT-116 (SN-38-high-sensitivity cells). The time-dependent profile (after exposure to SN-38) of the peak, visualized as a graph, exhibited characteristic variation. Thus, the peak was thought to be attributed to a metabolite relating to sensitivity to SN-38 (FIG. 8). The composition of the metabolite detected as the above peak was estimated by use of analysis software Analyst™ QS (Applied Biosystems, Inc.). From the data including the isotope ratio to a parent peak and precise mass, the composition of the substance detected at m/z of 104.070 was determined to be $C_4H_{10}NO_2$ (as ion). By use of KEGG PATHWAY (life system information integrated database (http://www.kegg.jp/) produced by Kyoto University, a substance assumed by the ion composition was retrieved. As a result, the peak was found to be attributed to γ-aminobutyric acid (GABA). Through investigation by use of a standard sample of GABA, the observed migration time in capillary electrophoresis was found to coincide with that of the standard sample.

The composition of the substance detected as a peak at m/z of 133.06 was estimated by use of analysis software Analyst™ QS (Applied Biosystems, Inc.). From the data including the isotope ratio to a parent peak and precise mass, the composition of the substance detected at m/z of 133.06 was determined to be $C_4H_8N_2O_3$ (as ion). By use of KEGG PATHWAY (life system information integrated database (http://www.kegg.jp/) produced by Kyoto University, a substance assumed by the ion composition was retrieved. As a result, the peak was found to be attributed to asparagine. Through investigation by use of a standard sample of asparagine, the observed migration time in capillary electrophoresis was found to coincide with that of the standard sample.

The composition of the substance detected as a peak at m/z of 134.04 was estimated by use of analysis software Analyst™ (Applied Biosystems, Inc.). From the data including the isotope ratio to a parent peak and precise mass, the composition of the substance detected at m/z of 134.04 was determined to be $C_4H_8NO_4$ (as ion). By use of KEGG PATHWAY (life system information integrated database (http://www.kegg.jp/) produced by Kyoto University, a substance assumed by the ion composition was retrieved. As a result, the peak was found to be attributed to aspartic acid. Through investigation by use of a standard sample of aspartic acid, the observed migration time in capillary electrophoresis was found to coincide with that of the standard sample.

Figure 12:
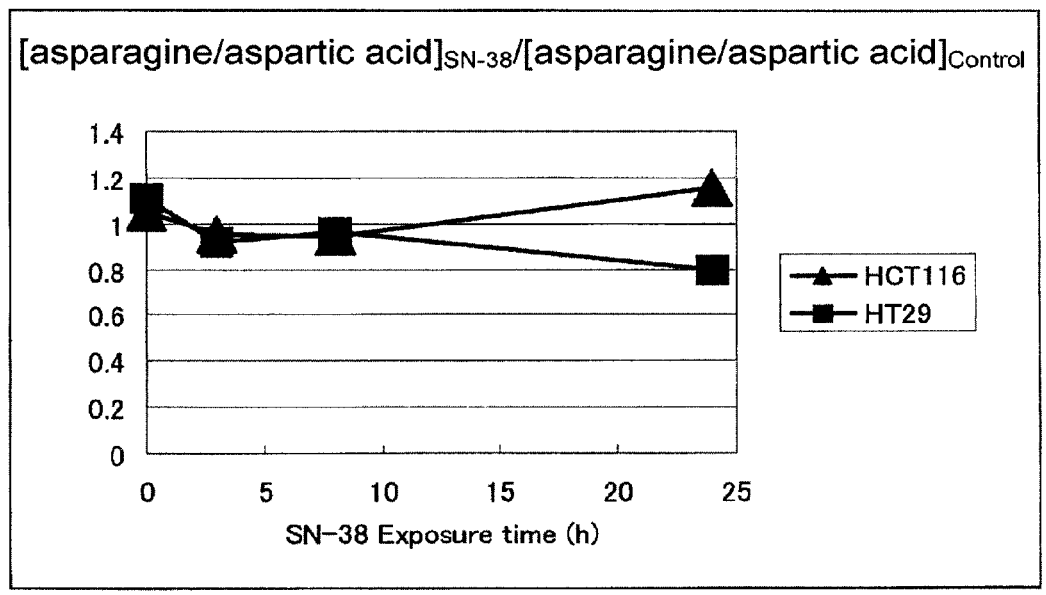

Furthermore, the ratio of asparagine level to aspartic acid level ([asparagine/aspartic acid]) was calculated. By dividing the [asparagine/aspartic acid] ratio obtained after exposure to SN-38 by the [asparagine/aspartic acid] ratio obtained without exposure thereto, the value [asparagine/aspartic acid]$_{SN-38}$/[asparagine/aspartic acid]$_{Control}$ was obtained. As a result, the value was found to considerably increase in HCT-116 (SN-38-high-sensitivity cells) and considerably decrease in HT-29 (SN-38-low-sensitivity cells) (FIG. 12).

Example 2

(1) Method
(a) Cells Employed

Eight human colorectal cancer cell lines (HCT-116, HT-29, HCT-15, Lovo, LS174T, SW480, SW620, and WiDr) were employed. HCT-116 and HT-29 were obtained from Kabushiki Kaisha Yakult Honsha. Lovo, SW480, and WiDr were obtained from Dainippon Sumitomo Pharma Co., Ltd. HCT-15 and LS174T were obtained from Cell Resource Center for Biomedical Research, Institute of Development, Aging and Cancer, Tohoku University. SW620 was obtained from Summit Pharmaceuticals International Corporation.

(b) Drugs

SN-38 powder was obtained from Kabushiki Kaisha Yakult Honsha. SN-38 was dissolved in DMSO, and, before use, the solution was diluted so that the DMSO concentration of each of the culture media employed in experiments was adjusted to 0.1% or less.

(c) Evaluation of Sensitivity of Cancer to SN-38

Cancer cells of each cell line were exposed to SN-38 (0 nmol/L to 5 μmol/L) for 72 hours. After exposure to SN-38, cell viability was determined by means of an MTS assay (CellTiter96™AQ$_{ueous}$ One Solution Cell Proliferation Assay, Promega). IC$_{50}$ (concentration of SN-38 at which 50% of cells in an SN-38-non-treated well are inhibited) was calculated for each cell line and employed as the sensitivity of the cell line to SN-38. Sensitivity determination of each cell line was performed in triplicate and twice.

(d) Recovery of Metabolites in the Bells

The medium was removed from a cell sample of each cell line in a steady state, and the cells were washed on ice with 5% mannitol (4° C.). Immediately thereafter, methanol (4° C., containing an internal standard) was added to the washed cells, to thereby inactivate present enzymes, and stored at −80° C. Separately, cells for cell count were provided in addition to the cells from which metabolites were extracted, and subjected to the above treatment and cell counting. The data were employed in correction of the cell counts. In each case, the experiment was carried out in triplicate and twice.

(e) Preparation of Metabolome Sample

Chloroform and Milli-Q water were added to the methanol solution stored at −80° C., and liquid-liquid extraction was performed, to thereby removed contaminants. A water-methanol layer containing metabolites was recovered and centrifugally filtered through an ultrafilter with a molecular weight cutoff of 5,000 Da, to thereby remove proteins. The filtrate was dried under reduced pressure and then stored at −80° C. The filtrate was dissolved in Milli-Q water immediately before the measurement and then subjected to metabolome measurement.

(f) Metabolome Measurement

Comprehensive analysis of intracellular metabolites was performed by means of a capillary electrophoresis-time-of-flight-type mass spectrometer (CE-TOFMS) (product of Agilent Technologies). In the comprehensive analysis of cationic metabolites, voltage was applied so that the outlet of the capillary served as a negative electrode, whereas in the comprehensive analysis of anionic metabolites, voltage was applied so that the outlet of the capillary served as a positive electrode. Metabolites detected at m/z values of 50 to 1,000 were simultaneously quantitated.

(g) Correlation Analysis Between GABA Level and Sensitivity to SN-38

Each cell sample was analyzed in terms of the peak attributed to GABA detected through CE-TOFMS. Specifically, correlation analysis was carried out between the peak area and $IC_{50}$ (50% inhibitory concentration) of each cell line.

(2) Results (a) Evaluation of Sensitivities of Eight Human Colorectal Cancer Cell Lines to SN-38

Figure 13:
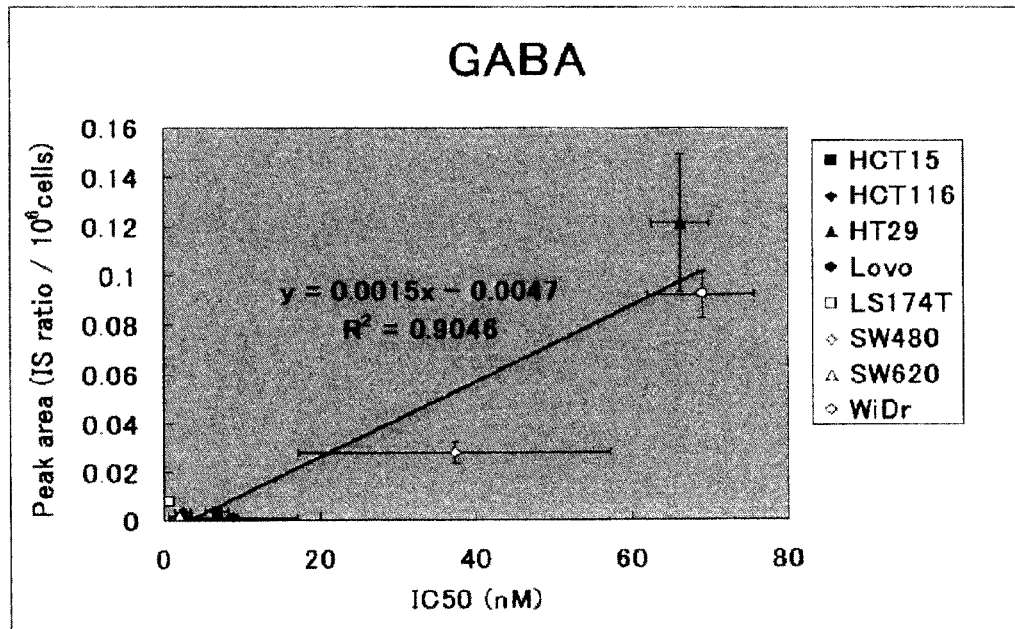

The $IC_{50}$ values of each cell lines were found to be 0.74±0.23 to 68.94±6.83 nmol/L, indicating a wide range of variation in sensitivity (FIG. 13).

(b) Correlation Analysis Between GABA Level and Sensitivity to SN-38

Each cell sample was analyzed in terms of the peak attributed to GABA detected through CE-TOFMS. Specifically, correlation analysis was carried out between the peak area and $IC_{50}$ of each cell line. As a result, high positive correlation was confirmed (FIG. 13).

Example 3

(1) Method

The experiment procedure of Example 2 was repeated twice. The data obtained in the experiments (three times in total) were further analyzed. Peaks detected through CE-TOFMS in the tested cell samples were compared with the data of 278 standard samples whose m/z values and migration times were already known, whereby 146 metabolites were identified in any of the tested cell samples. The 146 metabolites were investigated through single regression analysis in terms of the correlation between the intracellular content (in eight human colorectal cancer cell lines) and $Log[IC_{50}]$ of each cell line.

(2) Results (a) Evaluation of Sensitivities of Eight Human Colorectal Cancer Cell Lines to SN-38

Figure 14:
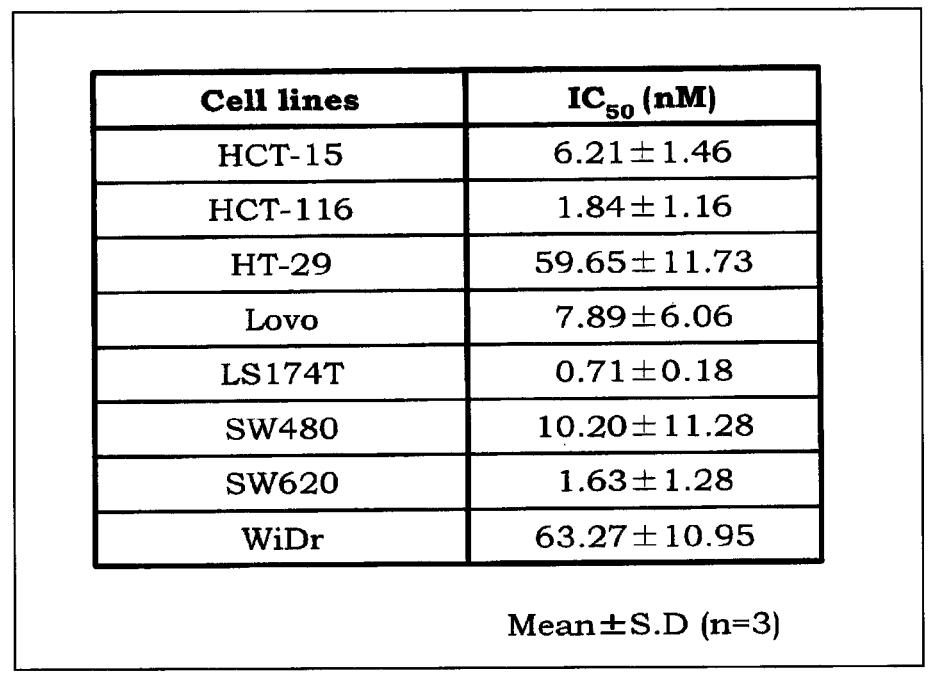

The sensitivity of each of eight human colorectal cancer cell lines (HCT-116, HT-29, HCT-15, Lovo, LS174T, SW480, SW620, and WiDr) was evaluated by employing $IC_{50}$ calculated through MTS assay as an index. As a result, WiDr exhibited the highest $IC_{50}$ (63.27±10.95 nM), indicating low sensitivity to SN-38. Meanwhile, LS174T exhibited the lowest $IC_{50}$ (0.71±0.18 nM), indicating high sensitivity to SN-38 (FIG. 14).

(b) Correlation Between the Intacellular Metabolite Content and Sensitivity to SN-38

Figure 15:
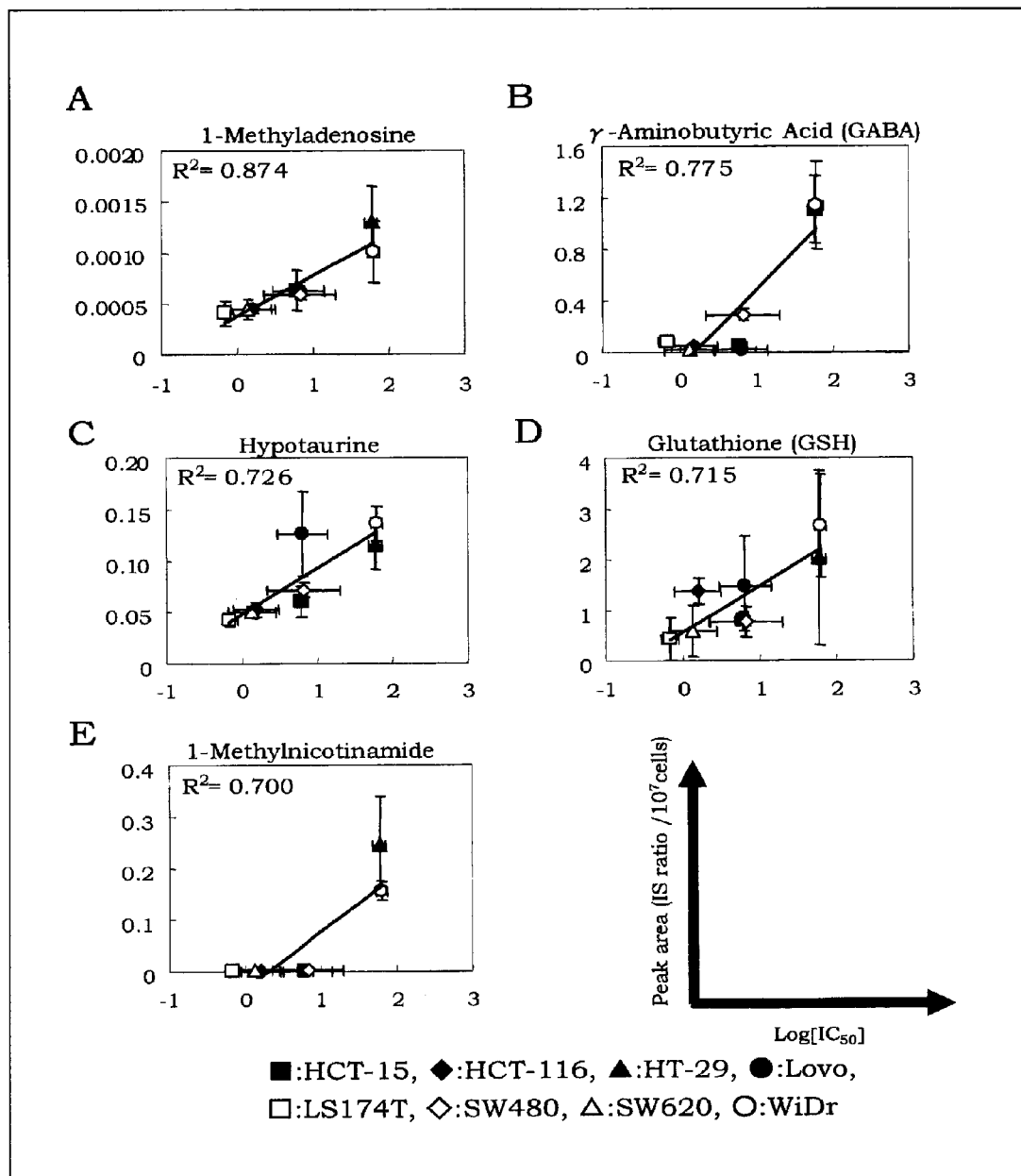

Metabolites were extracted from eight human colorectal cancer cell lines and were simultaneously analyzed through CE-TOFMS. The thus-obtained data were compared with the data of 278 standard samples which the laboratory of the present inventors possess. The 146 metabolites identified in any of the tested cell samples were investigated through single regression analysis in terms of the correlation between the intracellular content (in eight human colorectal cancer cell lines) and $Log[IC_{50}]$ of each cell line. As a result, significant correlation between the intracellular content and Log $[IC_{50}]$ was observed in the following metabolites: 1-methyladenosine, GABA, hypotaurine, glutathione (GSH), and 1-methylnicotinamide (p<0.01, $R^2$ 0.7) (FIG. 15). These metabolites exhibited a low intracellular level in SN-38-high-sensitivty cells and a high intracellular level in SN-38-low-sensitivity cells.

Figure 16:
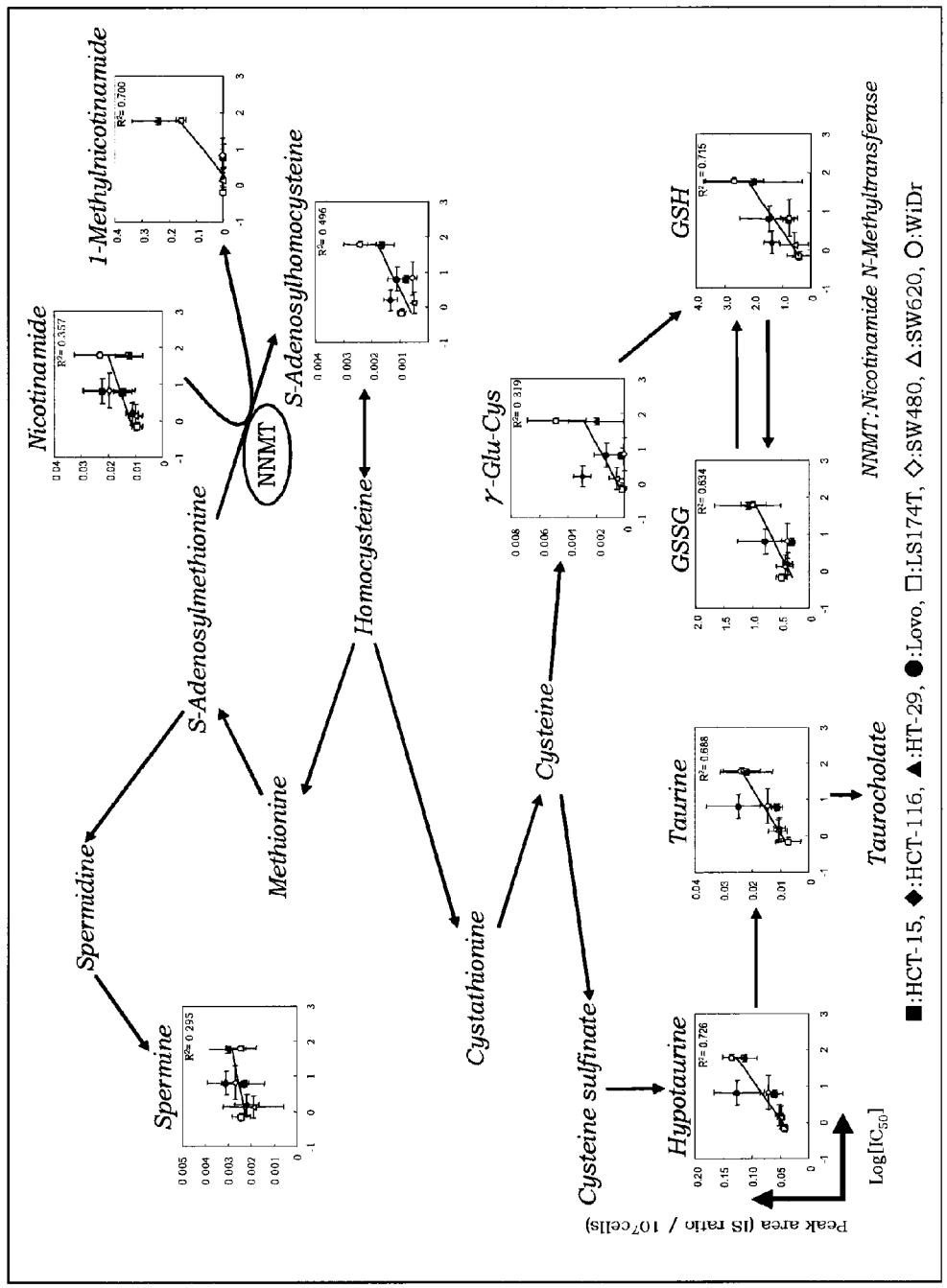

Furthermore, since glutathione-metabolism-related substances (hypotaurine, glutathione, and 1-methylnicotinamide) were found to have significant correlation between the intracellular content and sensitivity to SN-38, other glutathione-metabolism-related substances were investigated in terms of the correlation between the intracellular content and sensitivity to SN-38. As a result, in addition to hypotaurine, glutathione, and 1-methylnicotinamide, the correlation between the intracellular content and sensitivity to SN-38 was observed in taurin ($R^2$=0.688), glutathione disulfide (GSSG, $R^2$=0.634), S-adenosyl homocysteine ($R^2$=0.496), nicotinamide ($R^2$=0.357), γ-glutamyl cysteine (γ-Glu-Cys, $R^2$=0.319), and spermine ($R^2$=0.295) (FIG. 16).

The invention claimed is:

1. A method for determining sensitivity of a subject having colorectal cancer to an anti-cancer agent selected from the group consisting of irinotecan, a salt of irinotecan, SN-38, and a salt of SN-38, comprising measuring a level, in a specimen derived from the subject, of at least one substance selected from the group consisting of:

a substance detected as an anion at m/z of 149.05 to 149.06;
a fragment of a substance detected as an anion at m/z of 149.05 to 149.06;
a substance detected as an anion at m/z of 152.99 to 153.00;
a fragment of a substance detected as an anion at m/z of 152.99 to 153.00;
a substance detected as a cation at m/z of 724.34 to 724.35;
a fragment of a substance detected as a cation at m/z of 724.34 to 724.35;
glycerol 3-phosphate;
dihydrobiopterin;
GABA;
lactic acid;
asparagine;
aspartic acid;
2-methylbutyroylcarnitine;
1-methyladenosine; and
glutathione;
wherein a value of m/z is obtained by mass spectrometry.

2. The determination method of claim 1, wherein the specimen is a biological sample.

3. The determination method of claim 1, wherein the specimen is a biological sample derived from the subject, to which subject an anti-cancer agent has been administered.

4. The determination method of claim 1, wherein the anti-cancer agent is irinotecan or a salt of irinotecan.

5. The determination method of claim 1, wherein the anti-cancer agent is SN-38, or a salt of SN-38.

6. A kit which performs the determination method of claim 1, comprising a protocol for measuring the level, in the specimen derived from the subject, of at least one substance selected from the group consisting of:
- a substance detected as an anion at m/z of 149.05 to 149.06;
- a fragment of a substance detected as an anion at m/z of 149.05 to 149.06;
- a substance detected as an anion at m/z of 152.99 to 153.00;
- a fragment of a substance detected as an anion at m/z of 152.99 to 153.00;
- a substance detected as a cation at m/z of 724.34 to 724.35;
- a fragment of a substance detected as a cation at m/z of 724.34 to 724.35;
- glycerol 3-phosphate;
- dihydrobiopterin;
- GABA;
- lactic acid;
- asparagine;
- aspartic acid;
- 2-methylbutyroylcarnitine;
- 1-methyladenosine; and
- glutathione, wherein a value of m/z is obtained by mass spectrometry.

7. The kit of claim 6, wherein the specimen is a biological sample.

8. The kit of claim 6, wherein the specimen is a biological sample derived from the subject, to which subject an anti-cancer agent has been administered.

9. The kit of claim 6, wherein the anti-cancer agent is irinotecan or a salt of irinotecan.

10. The kit of claim 6, wherein the anti-cancer agent is SN-38, and or a salt of SN-38.

11. The determination method of claim 1, comprising measuring a level of asparagine and a level of aspartic acid in the specimen, and calculating a ratio of the level of asparagine to the level of aspartic acid.

12. The determination method of claim 1, further comprising measuring a level of the substance involved in a metabolic pathway of glutathione in the specimen, wherein the substance is at least one selected from the group consisting of glutathione, hypotaurine, 1-methylnicotinamide, taurine, glutathione disulfide, S-adenosyl homocysteine, nicotinamide, γ-glutamyl cysteine, and spermine.

* * * * *